United States Patent
Ishii et al.

(10) Patent No.: US 11,642,380 B2
(45) Date of Patent: May 9, 2023

(54) PRODUCTION METHOD OF NASAL DROP COMPOSITION, AND NASAL DROP COMPOSITION

(71) Applicant: WELL STONE CO., Miyazaki (JP)

(72) Inventors: Yoichi Ishii, Miyazaki (JP); Takeshi Okamoto, Miyazaki (JP); Sayaka Makino, Miyazaki (JP)

(73) Assignee: WELL STONE CO., Miyazaki (JP)

( * ) Notice: Subject to any disclaimer, the term of this patent is extended or adjusted under 35 U.S.C. 154(b) by 144 days.

(21) Appl. No.: 17/361,684

(22) Filed: Jun. 29, 2021

(65) Prior Publication Data

US 2021/0322487 A1    Oct. 21, 2021

Related U.S. Application Data

(62) Division of application No. 16/485,220, filed as application No. PCT/JP2018/010580 on Mar. 16, 2018, now Pat. No. 11,077,152.

(30) Foreign Application Priority Data

Mar. 21, 2017  (JP) .............................. JP2017-054773

(51) Int. Cl.
   *A61K 35/62* (2006.01)
   *A61P 11/12* (2006.01)

(52) U.S. Cl.
   CPC .............. *A61K 35/62* (2013.01); *A61P 11/12* (2018.01)

(58) Field of Classification Search
   None
   See application file for complete search history.

(56) References Cited

U.S. PATENT DOCUMENTS

| | | | |
|---|---|---|---|
| 5,186,944 | A | 2/1993 | Ishii et al. |
| 2013/0045921 | A1 | 2/2013 | Endo |
| 2014/0243271 | A1 | 8/2014 | Endo |
| 2017/0007673 | A1 | 1/2017 | Endo |
| 2018/0318395 | A1 | 11/2018 | Endo |
| 2019/0060215 | A1 | 2/2019 | Ishii et al. |
| 2019/0365639 | A1 | 12/2019 | Ishii et al. |
| 2020/0093868 | A1 | 3/2020 | Ishii et al. |

FOREIGN PATENT DOCUMENTS

| | | |
|---|---|---|
| CN | 102144722 | 8/2011 |
| CN | 102641380 | 8/2012 |
| CN | 103830535 | 6/2014 |
| JP | 4591810 | 9/2010 |
| JP | 4790096 | 7/2011 |
| JP | 2012-197193 | 10/2012 |
| JP | 2013-180995 | 9/2013 |
| JP | 2015-93818 | 5/2015 |
| JP | 6100411 | 3/2017 |
| KR | 100765909 | 10/2007 |

OTHER PUBLICATIONS

International Search Report (ISR) dated Apr. 24, 2018 in International (PCT) Application No. PCT/JP2018/010580.
"Environmental Protection Science", Production of High-efficiency Deodorant from Earthworm Feces Pellets, Jan. 31, 1992, vol. 18, No. 1, Translated by Zhaofu Zhang from a Japanese magazine "Latest Technical Information", 1990, No. 2.
Liu et al., "Technologies for Well-off in rural China", Valuable Earthworm Feces Pellets, Jun. 30, 2001, Issue No. 6.

*Primary Examiner* — Ralph J Gitomer
(74) *Attorney, Agent, or Firm* — Wenderoth, Lind & Ponack, L.L.P.

(57) ABSTRACT

Provided are: a method for producing a nasal drop composition suitable for treatment or prevention of a disease or symptom in the nasal cavities; and a nasal drop composition produced by the production method. The nasal drop composition production method characterized by including a mixing step of mixing earthworm castings with water and a collecting step of collecting vaporized water generated from a mixture obtained in the mixing step to obtain a liquid; and the nasal drop composition produced by the production method. It is preferred to further mix an organic substance together with the earthworm castings and the water in the mixing step.

5 Claims, No Drawings

PRODUCTION METHOD OF NASAL DROP COMPOSITION, AND NASAL DROP COMPOSITION

TECHNICAL FIELD

The present invention relates to: a method for producing a nasal drop composition suitable for treatment or prevention of a disease or symptom in the nasal cavities; and a nasal drop composition produced by the production method.

BACKGROUND ART

Conventionally, a nasal drop composition is used for treatment or prevention of pollinosis and empyema. Nasal drop compositions have been variously studied (for example, Patent Documents 1 and 2), but, generally speaking, a nasal drop composition different from conventional ones is demanded due to difficulties in obtaining a desired effect according to a target.

RELATED ART DOCUMENTS

Patent Document

Patent Document 1 JP4591810B2
Patent Document 2 JP4790096B2

SUMMARY OF THE INVENTION

Problems to be Solved by the Invention

In these situations, an object of the present invention is to provide: a method for producing a nasal drop composition suitable for treatment or prevention of a disease or symptom in the nasal cavities; and a nasal drop composition produced by the production method.

Means for Solving the Problems

The present inventors intensively studied to solve the above-described problems and consequently discovered that, a liquid obtained by collecting vaporized water generated upon mixing of earthworm castings with water is suitable for treatment or prevention of a disease or symptom in the nasal cavities, thereby completing the present invention.

Namely, a nasal drop composition production method according to the present invention is characterized by including: a mixing step of mixing earthworm castings with water; and a collecting step of collecting vaporized water generated from a mixture obtained in the mixing step to obtain a liquid.

In the nasal drop composition production method according to the present invention, it is preferred to further mix an organic substance together with the earthworm castings and the water in the mixing step.

In the nasal drop composition production method according to the present invention, it is preferred that the organic substance is a wood material.

It is preferred that the nasal drop composition production method according to the present invention further includes a diluting step of diluting the liquid obtained by the collection of the vaporized water in the collecting step with water.

A nasal drop composition according to the present invention is characterized by being produced by the nasal drop composition production method.

It is preferred that the nasal drop composition according to the present invention is used in the form of mist.

It is preferred that the nasal drop composition according to the present invention is for treatment or prevention of a disease or symptom in the nasal cavities.

In the nasal drop composition according to the present invention, it is preferred that the disease or symptom in the nasal cavities is pollinosis or empyema.

A method of treating pollinosis or empyema according to the present invention is characterized by administering the nasal drop composition to a patient.

It is preferred that the nasal drop composition according to the present invention is for use in the treatment of pollinosis or empyema.

Effects of the Invention

According to the present invention, it is possible to provide: a method for producing a nasal drop composition suitable for treatment or prevention of a disease or symptom in the nasal cavities; and a nasal drop composition produced by the production method.

Mode for Carrying Out the Invention

The nasal drop composition production method according to the present invention is characterized by including: a mixing step of mixing earthworm castings with water; and a collecting step of collecting vaporized water generated from a mixture obtained in the mixing step. In the mixing step, it is preferred that an organic substance is further mixed together with the earthworm castings and the water. Although details about the mechanism is not known clearly, it is believed that microorganisms such as bacteria contained in earthworm castings decompose and ferment organic substances contained in the earthworm castings and organic substances added separately to the earthworm castings and, as a result, a liquid obtained by collecting the vaporized water is effective for treatment or prevention of a disease or symptom in the nasal cavities.

Hereinbelow, the nasal drop composition production method and the nasal drop composition according to the present invention will be described in detail.

[Nasal Drop Composition Production Method]
(Mixing step)

The mixing step is a step of mixing earthworm castings with water.

The earthworm castings are not particularly limited, and castings of earthworms *Lumbricus rubellus*, *Lumbricus terrestris* (LT), *Eisenia foetida*, *Allolobophora caliginosa*, *Dendrobaena octaedra*, *Allolobophora japonica* Michaelsen, *Drawida hattamimizu* Hatai, *Pheretima divergens* Michaelsen, *Pheretima communissima*, *Pheretima agrestis*, *Pheretima sieboldi* Horst, *Pheretima hilgendorfi*, *Pontodrilus matsushimensis* Iizuka, *Tubifex hattai* Nomura, and *Limnodrilus gotoi* Hatai (=*L. socialis* Stephenson) can be used.

The water to be mixed with the earthworm castings is not particularly limited, and tap water and distilled water can be used. The water may be purified with a filtration material, a reverse osmosis membrane or the like. From the viewpoint of the removal of microorganisms such as bacteria, it is preferred to use a microporous filtration material, a microporous reverse osmosis membrane or the like. For example, an SPG (Shirasu porous glass) permeable membrane can be used preferably.

The mixing ratio of the earthworm castings and the water is preferably 0.05 to 20 L, more preferably 0.1 to 10 L, still more preferably 0.2 to 5 L, particularly preferably 0.5 to 2 L of the water with respect to 1 kg of the earthworm castings.

In the mixing step, it is preferred that an organic substance is further mixed together with the earthworm castings and the water. When an organic substance is mixed, a nasal drop composition more excellent in the effect of treating or preventing a disease or symptom in the nasal cavities can be obtained, and the pH value of the nasal drop composition can be controlled. The organic substance is not particularly limited, as long as the organic substance can be decomposed when mixed with the earthworm castings, but for example, an organic substance derived from a living organism such as an animal, a plant, a bacterium or a protozoan can be used. Specific examples of a plant-derived organic substance include: a wood material such as wood chips, wood dusts and rice hulls; a mushroom bed for use in the culturing of mushrooms; and the like. To mix a wood material as the organic substance is preferred, because an odorless liquid is likely to be collected in the collecting step. As the wood material, wood chips are preferred. The species of the wood is not particularly limited, and examples thereof include a conifer tree such as yew, Japanese torreya, Japanese cypress, hiba arborvitae, Japanese cedar, Japanese umbrella pine, pine, Japanese Douglas fir, hondo spruce, fir, hemlock fir, or sequoia, or a broadleaf tree such as Japanese cherry, oak, zelkova, beech, birch, chinquapin, maple, alder, Japanese linden, Japanese hornbeam, or bamboo. Among the wood, wood of Pinales can suitably be used. More preferably, wood of Cupressaceae can be used, still more preferably, wood of Taxodioideae can be used, and particularly preferably, wood of Cryptomeria can be used.

The mixing ratio of the earthworm castings and the organic substance is preferably 0.05 to 20 kg, more preferably 0.1 to 10 kg, still more preferably 0.2 to 5 kg, and particularly preferably 0.5 to 2 kg of the organic substance with respect to 1 kg of the earthworm castings.

The mixing method to be employed in the mixing step is not particularly limited, and it is preferred that the mixture is fully mixed by stirring or the like. The order in which the components are mixed is not particularly limited. For example, it is possible to introduce the earthworm castings and the organic substance into a vessel and subsequently add water thereto, and it is also possible to introduce the organic substance into a vessel, subsequently add water thereto, and subsequently add the earthworm castings thereto.

It is not necessary to mix the whole amounts of the components at once, but each of the water, the earthworm castings and/or the organic substance may be added in divided several portions during the mixing. Adding each component in several portions is preferred, because it is possible to continuously collect vaporized water while replenishing the water that is reduced by vaporization and the earthworm castings or the organic substance that is reduced by decomposition.

In addition, the fermentation is further stabilized after a lapse of time from the first mixing procedure. Therefore, it is preferred to collect the vaporized water, for example, after a lapse of about 1 day to obtain a liquid excellent in an effect of treatment or prevention of a disease or symptom in the nasal cavities. From this view point, it is preferred to continuously collect the vaporized water while replenishing the components in several portions.

Heat is generated in the mixture as the result of the fermentation of the earthworm castings and the separately added organic substance. However, at some air temperatures, it is preferred to mix the components while heating. When heating the mixture, it may be heated, for example, to 30 to 50° C.

(Collecting Step)

The collecting step is a step of collecting vaporized water generated from the mixture obtained in the mixing step to obtain a liquid (hereinafter, also referred to as "aqueous organic substance decomposition product"). The collecting step may be carried out while carrying out the mixing step.

In the collecting step, vaporized water generated in a temperature range rising due to a fermentation heat (reaction heat) generated as a result of the fermentation of the mixture can be collected, and it is not necessary to heat the mixture up to the boiling point. Depending on the temperatures, it is preferred to mix the components while heating. When heating the mixture, it may be heated, for example, to 30° C. to 50° C.

The method for the collecting is not particularly limited, as long as vaporized water can be collected. For example, vaporized water may be collected with a dehumidifier. As the dehumidifier, a cooling-mode dehumidifier, a compression-mode dehumidifier or the like can be used. It is preferred to collect vaporized water without boiling the mixture.

The method for making the collected vaporized water into a liquid is not particularly limited. For example, when the vaporized water is collected with a dehumidifier, an aqueous organic substance decomposition product can be obtained. The dehumidifier is not particularly limited, as long as the vaporized water can be collected in a liquid form. For example, a cooling-mode dehumidifier, a compression-mode dehumidifier or the like can be used.

The pH value of the liquid obtained by the collection of the vaporized water is preferably 5 to 9, more preferably 6 to 8, still more preferably 6.5 to 7.5.

(Diluting Step)

The aqueous organic substance decomposition product obtained by the collection of the vaporized water in the collecting step may be used as the nasal drop composition without any modification. However, it is preferred to use the aqueous organic substance decomposition product in a diluted form. A solvent to be used for the dilution may be water, and tap water and distilled water can be used. The water to be used for the dilution may be purified with a filtration material, a reverse osmosis membrane and the like. From the viewpoint of the removal of microorganisms such as bacteria, it is preferred to use a microporous filtration material, a microporous reverse osmosis membrane or the like, and an SPG (Shirasu porous glass) permeable membrane is preferably used. In the case where the aqueous organic substance decomposition product is diluted, the dilution may be carried out at a dilution factor of, for example, 1.5 to 10 times, preferably 4 to 6 times, more preferably 4.5 to 5.5 times.

[Nasal drop composition]

A nasal drop composition according to the present invention is characterized by being produced by the nasal drop composition production method according to the present invention. The nasal drop composition according to the present invention is not particularly limited as long as the nasal drop composition is produced by the nasal drop composition production method according to the present invention and is effective for treatment or prevention of a disease or symptom in the nasal cavities, and is preferably in a liquid form. Alternatively, the liquid nasal drop composition may be sprayed or evaporated in the form of mist. Furthermore, the nasal drop composition may be processed into a solid form such as gel, powder, granule or the like by mixing with, for example, an excipient or the like.

The nasal drop composition of the present invention may contain a pharmaceutically acceptable carrier. As a pharmaceutically acceptable carrier, an excipient, a binder, a disintegrant, a fluidizing agent, a lubricant, a coating agent, a suspending agent, a coloring agent, a sweetening agent, a surfactant, or the like can be used, and the composition can be made in the form of a general pharmaceutical preparation according to a known method. The composition may also contain another therapeutic/prophylactic ingredient or a pharmaceutically acceptable additive.

In the nasal drop composition of the present invention, the blending amount of the liquid collected in the collecting step may be an amount to be effective according to each purpose. An appropriate blending amount depends on various factors such as a purpose, a form, production conditions and the like, and for example, in the case of a liquid nasal drop composition, the amount of the liquid collected in the collecting step may be 5% by volume or more, preferably 5 to 50% by volume, more preferably 10 to 40% by volume, and still more preferably 20 to 30% by volume.

The amount of the nasal drop composition of the present invention to be used also may be an amount effective for the purpose. The appropriate amount to be used depends on various factors such as a purpose, a form, production conditions, symptoms, and the like, and, for example, when a liquid nasal drop composition is used by spraying in the form of mist in the nasal cavities, spraying may be performed 6 to 10 times per day.

The nasal drop composition of the present invention is preferably used for treatment or prevention of a disease or symptom in the nasal cavities. The disease or symptom in the nasal cavities is not particularly limited, and examples thereof include pollinosis and empyema.

In the nasal drop composition according to the present invention, other active ingredients and known conventional additives usable in nasal drop compositions (e.g., a coloring agent, a fragrance, an antioxidant agent, an ultraviolet ray absorber, a chelating agent, a surfactant, a viscosity modifier, a pH modifier, a thickening agent, an antifoaming agent, a preservative agent, an bactericidal/antibacterial agent, a dispersant and an organic solvent) may be added, as long as the advantageous effects of the present invention cannot be deteriorated.

The nasal drop composition of the present invention may contain dry powder, milled matter and/or extract of earthworm. By mixing dry powder, milled matter, and/or extract of earthworm, it is possible to obtain a liquid more excellent in the effect of treatment or prevention of a disease or symptoms in the nasal cavities. Among these, an extract of earthworm is more preferable, since a more excellent effect can be obtained. As the earthworm extract, an extract extracted from a dried earthworm powder with water, ethanol or an aqueous ethanol solution can be used, for example.

Earthworms used as a raw material are not particularly limited, and, for example, *Lumbricus rubellus, Lumbricus terrestris, Eisenia foetida, Allolobophora caliginosa, Dendrobaena octaedra, Allolobophora japonica* Michaelsen, *Drawida hattamimizu* Hatai, *Pheretima divergens* Michaelsen, *Pheretima communissima, Pheretima agrestis, Pheretima sieboldi* Horst, *Pheretima hilgendorfi, Pontodrilus matsushimensis* Iizuka, *Tubifex hattai* Nomura, *Limnodrilus gotoi* Hatai (=*L. socialis* Stephenson), or the like can be used.

The dry earthworm powder herein means powder obtained by drying a milled matter or extract of untreated or pretreated earthworms. The milled matter of earthworms is a liquid or paste-like one obtained by milling untreated or pretreated earthworms. The extract of earthworms means an extract obtained by dissolving untreated or pretreated earthworms or milled matter thereof in water or an organic solvent and by removing or separating an insoluble fraction therefrom. The pretreatment is not particularly limited, and examples thereof include a removal treatment of dirt or the like described below. The dry powder, milled matter, and extract of earthworm may be subjected to post-treatment, and examples of the post-treatment include granulation, filtration, purification, concentration, dilution, and pH adjustment.

The milling method for obtaining milled earthworms is not particularly limited, and earthworms can be ground using a homogenizer, a blender, a homomixer, a grinder, a Dounce homogenizer, or the like.

An extraction method for obtaining an extract of earthworms is not particularly limited, but, for example, an extraction can be extracted by dissolving dry powder or a milled matter of earthworms in an extraction solvent and by removing or separating an insoluble fraction therefrom. Examples of the extraction solvent include water, an aqueous solution and an organic solvent such as ethanol, acetone or ethyl acetate, and the extraction solvent may be used singly or two or more thereof may be used in combination. Among them, water, ethanol or aqueous ethanol solution is preferable.

A drying method for obtaining a dried earthworm is not particularly limited, and the dried earthworm can be obtained by a drying method such as freeze drying, heat drying, or spray drying. Among them, the freeze drying is preferred for the reasons described below.

It is preferable to remove contents remaining in the gastrointestinal tract of an earthworm, dirt adhering to a skin thereof and the like. The removal method is not particularly limited, and a known method may be used for removal. For example, a method in which an earthworm is immersed in an aqueous solution of an alkaline salt such as sodium salt or potassium salt to discharge contents in the gastrointestinal tract (the method described in JP Nos. H01-47718A, H01-47719A, H01-47720A, or H01-268639A), a method in which an earthworm is allowed to stand in an acid aqueous solution maintained at 6 to 26° C. for 0.1 to 5 hours to remove contents in the gastrointestinal tract (the method described in JP No. H03-72427A), or the like may be employed.

As such a removal method, it is preferable to bring an earthworm into contact with a chloride of a metal described below and/or hydroxycarboxylic acid.

A chloride of the metal is a chloride of at least one metal selected from the group consisting of potassium, sodium, magnesium and calcium. In other words, the chloride of metal is at least one selected from the group consisting of potassium chloride, sodium chloride, magnesium chloride and calcium chloride. A mixture of these may also be used or a mixture of these with other harmless components that can be added to food may be used. Examples of such a mixture include salt, rock salt and solar salt. A chloride of the above-described metal can be used by sprinkling in a powdery form on a living earthworm, whereby the earthworm is in contact with the metal chloride.

It is preferable to bring a living earthworm into contact with hydroxycarboxylic acid as described below after bringing the living earthworm into contact with a chloride of the above-described metal. It is also possible to bring the earthworm into contact with hydroxycarboxylic acid as described below without contacting the earthworm with a chloride of the above-described metal.

The contact with hydroxycarboxylic acid can also be carried out by sprinkling powdery hydroxycarboxylic acid on living earthworms. The living earthworms may be immersed in a hydroxycarboxylic acid aqueous solution having a pH of 2 to 5. When contacting living earthworms with hydroxycarboxylic acid after contact with a metal chloride, it is preferable that the contact with hydroxycarboxylic acid be carried out promptly after the contact with the chloride of the metal. It is preferable to wash the living earthworms with water before the contact with the hydroxycarboxylic acid. By contacting the earthworms with hydroxycarboxylic acid after the removal of the chloride of the metal through water washing, earthworm dry powder having high enzyme activity is obtained. In the case of washing a metal chloride with water prior to contact with hydroxycarboxylic acid, the washing should be carried out preferably within 30 minutes, more preferably within 20 minutes after the start of contact with the metal chloride. The washing method is not particularly limited, and a known method can be adopted.

When living earthworms are kept in contact with hydroxycarboxylic acid powder for a long time, they die, they lose their living functions, and do not excrete intestinal contents in the gastrointestinal tract, and therefore, it is preferable to adjust the pH to 2 to 5 by diluting the hydroxycarboxylic acid with water as soon as possible, preferably within 30 seconds, more preferably within 20 seconds.

Because hydroxycarboxylic acid forms an unpleasant living environment for earthworms, living earthworms try to improve the living environment by releasing body fluids and excreta by self-preservation instinct. Since hydroxycarboxylic acid has bactericidal properties, hydroxycarboxylic acid plays a role of promoting the earthworms to excrete intestinal contents and the like remaining in the digestive organ as described above, and hydroxycarboxylic acid can be expected to have an effect of sterilizing germs attached to the earthworms.

The crystalline hydroxycarboxylic acid used in the above-described method can be used irrespective of the number of hydroxy groups or the number of carboxyl groups as long as the crystalline hydroxycarboxylic acid shows a crystalline form under the conditions of use. In other words, any of monohydroxy monocarboxylic acid, monohydroxy polycarboxylic acid, polyhydroxy monocarboxylic acid and polyhydroxy polycarboxylic acid may be used.

Examples of the hydroxycarboxylic acid include glycolic acid, lactic acid, acetic acid, β-hydroxypropionic acid, α-hydroxy-n-butyric acid, β-hydroxy-n-butyric acid, α-hydroxy-n-valeric acid, β-hydroxy-n-valeric acid, malic acid, α-methyl malic acid, α-hydroxy glutaric acid, β-hydroxy glutaric acid, citric acid, malonic acid, and succinic acid. Among them, lactic acid, acetic acid, malic acid, citric acid, malonic acid, and succinic acid are preferable because they can be used for food and are easily available. The hydroxycarboxylic acid may be used singly or two or more thereof may be used in a mixture.

Water accounts for 65% of the tissues of a living earthworm. There is a certain amount of time while the life-keeping function of a living earthworm lasts, but as the living earthworm dies, an enzyme works, and therefore, it is necessary to carefully control the time to leave the living earthworm in an uncomfortable living environment. Although such time depends on conditions, it is usually in a range of 3 to 180 minutes.

It is preferable that a living body of an earthworm treated with hydroxycarboxylic acid is washed with water and then milled to obtain a liquid or pasty milled matter. The washing is preferably performed with pure water. The washing method is not particularly limited, and a known water washing method can be adopted. The total time of a treatment process before milling, that is, the time from the sprinkling of a metal chloride on living earthworms to the completion of removal of hydroxycarboxylic acid by washing with water is preferably within 240 minutes.

The above-described milling method is not particularly limited, and for example, milling is carried out usually at 1 to 25° C. using, for example, a homogenizer, a blender, a homomixer, a grinder or a Dounce homogenizer. From the viewpoint of suppressing decomposition of earthworm components, it is preferable to carry out the milling at low temperature, and a temperature of 2 to 15° C. is preferable.

A milled matter obtained by milling earthworms are placed on a stainless steel tray or the like and subjected to freeze drying. At this time, since an enzyme contained in a living body of earthworm does not act on living cells but acts instantaneously on dead cells, there is a possibility that a putrefactive gas may be generated. In order to prevent this, it is preferable to instantaneously quench and freeze to −18° C. to −35° C. to suppress the action of the enzyme and then perform freeze-drying.

As described above, it is preferable to quickly freeze earthworms in order to make the earthworms into powder without impairing the inherent pharmacological action of the earthworms, but on the other hand, when the milled earthworms are frozen in a very short time, impurities that are present together with protein, which is the main component of an earthworm paste, form a spot-like unfrozen part, and may not be separated, and therefore, excessively rapid freezing is not preferable. Therefore, the freezing is preferably carried out at a low temperature of −18° C. to −35° C. for 20 to 240 hours, and more preferably 50 to 170 hours.

When performing the freeze-drying, it is important to choose the conditions under which moisture and impurities can be removed without remaining. For that purpose, it is preferable to control that the freeze-drying is performed under a pressure of 50 Pa or lower while increasing the temperature stepwise in a range of −60° C. to +90° C. for 10 to 60 hours.

In a method of the freeze-drying, for example, as described above, after a milled matter is frozen at a temperature of −18° C. to −35° C. for 20 to 240 hours, the temperature is then raised in several steps at a temperature of −60° C. to +90° C., and the milled matter is frozen vacuum dried for 10 to 60 hours while reducing the pressure in several stages at a pressure of 25 to 40 Pa, whereby a light yellow earthworm dry powder in a sterile state can be obtained.

Furthermore, it is preferable to include a step of dissolving the milled matter in a freeze-dried form in water or an aqueous ethanol solution and removing or separating an insoluble fraction. The step of removing or separating an insoluble fraction can be carried out as in the above through precipitation by leaving, centrifugation, filtration or the like. A step of dissolving the freeze-dried milled matter in water or an aqueous ethanol solution is preferably carried out with stirring or shaking. Time required for the dissolution is preferably 1 to 120 minutes, and more preferably 5 to 80 minutes. An ethanol concentration of the aqueous ethanol solution is not particularly limited; but it is preferably 10 to 70% (v/v), and more preferably 30 to 60%.

As an earthworm extract, a supernatant of a solution obtained by dissolving the freeze-dried earthworm milled matter in water or an aqueous ethanol solution as described above may be used as it is in the form of an aqueous solution, may be used as a concentrate after evaporating water therefrom, or may also be used in the form of powder by drying. A powder obtained by drying the supernatant may be dissolved in water and used. Alternatively, a powder obtained by freeze-drying an earthworm paste may be used as it is without being dissolved in water or an aqueous ethanol solution.

In the removal method for removing intestinal contents of an earthworm and dirt adhered to an earthworm skin, prior to a process of placing living earthworms in an unpleasant environment, that is, before bringing the living earthworms into contact with a metal chloride or hydroxycarboxylic acid, it is preferable that the living earthworms are placed in a flat box like a bread box, and that the living earthworms are left to stand for 10 to 50 hours in a light place to remove dirt adhering to their skin. The time to leave the living earthworms in the light place is more preferably 12 to 24 hours. In this process, the amount of the earthworms contained in the flat box is preferably such an amount that the earthworms are piled up to a thickness of 30 to 60 mm, and preferably 40 to 50 mm. It is preferable that there is no foreign matter such as sand or mud in this flat box, and since earthworms are nocturnal, living activities become active in dark places and earthworms may exhaust their physical strength, and therefore, keeping the interior of the flat box bright at night using an electric light culture method or the like is preferable. By this treatment, the living earthworms exert self-defense instinct and try to maintain the environment by excreting contents remaining in their gastrointestinal tracts, covering their entire body with these excreta, and thereby preventing evaporation of moisture. Thus, by repeatedly peeling off the dirt, namely excreta, covering the earthworms by appropriate means, it is possible to finally eliminate the contents in the gastrointestinal tract of the earthworms and the dirt adhering to the skin.

Peeling off of the dirt adhering to the skins of earthworms can be carried out, for example, by covering the living earthworms with a nonwoven fabric and adsorbing the dirt on the fabric. By combining: leaving the earthworm in the light place and removing the dirt adhering to the skins; and bringing the living earthworms into contact with a chloride of the above-described metal and/or hydroxycarboxylic acid, further excretion and removal of toxic substances from the earthworm bodies can be expected.

In the present invention, as a method for obtaining dry earthworm powder, the following methods are preferable particularly from the viewpoint of storage stability of the resulting dry powder.

(A-1) A method for producing dry earthworm powder including steps of:
bringing a living earthworm into contact with a chloride of at least one metal selected from the group consisting of potassium, sodium, magnesium, and calcium,
subsequently bringing the living earthworm into contact with a powdery hydroxycarboxylic acid, diluting the hydroxycarboxylic acid with water to adjust the pH to 2 to 5, leaving the earthworm in the diluted hydroxycarboxylic acid for 3 to 180 minutes, washing the earthworm with water, milling the earthworm, and freeze-drying the obtained milled matter.

(A-2) A method for producing dry earthworm powder including steps of:
bringing a living earthworm into contact with a chloride of at least one metal selected from the group consisting of potassium, sodium, magnesium, and calcium,
subsequently immersing the living earthworm in a hydroxycarboxylic acid aqueous solution in which the pH is adjusted to 2 to 5, leaving the earthworm in the solution for 3 to 180 minutes, washing the earthworm with water, milling the earthworm, and freeze-drying the obtained milled matter.

(A-3) A method for producing a dry earthworm powder further including in the (A-1) or (A-2) steps of: dissolving the freeze-dried milled matter in water or an aqueous ethanol solution, removing or separating an insoluble fraction therefrom, and then further freeze-drying the obtained solution.

After freeze-drying the milled matter obtained by grinding the living earthworm, the dried product obtained may be heat-treated from the viewpoint of sterilization of the dried product. The temperature of the heat treatment is preferably 110° C. or more and less than 130° C. When the heating temperature is lower than 110° C., sterilization of the dried product may be insufficient, and when the heating temperature is 130° C. or higher, an enzyme contained in the dried earthworm product is deactivated and the activity is unfavorably lowered. More preferably, the heating temperature is 115 to 125° C. The heating method is not particularly limited, and examples thereof include a method of applying hot air, a method of using a heating jacket, a method of heating the subject on a tray or the like using a heater, and a method using a thermostat incubator. The heating time is preferably 30 seconds to 130 minutes, more preferably 30 minutes to 90 minutes, and still more preferably 60 minutes to 90 minutes. When the heating time is too short, sterilization may be insufficient, and when the heating time is too long, the activity of the enzyme will be lost, which is not preferable. Since the enzymatic activity is lost when the enzyme in the liquid is subjected to the heat treatment, it is preferable to perform the heat treatment on the dry earthworm powder.

In the present invention, as a method for obtaining a milled matter of an earthworm, the following methods are preferable.

(B-1) A method for producing a milled matter of an earthworm including steps of:
bringing a living earthworm into contact with a chloride of at least one metal selected from the group consisting of potassium, sodium, magnesium, and calcium,
subsequently bringing the living earthworm into contact with a powdery hydroxycarboxylic acid, diluting the hydroxycarboxylic acid with water to adjust the pH to 2 to 5, leaving the earthworm in the diluted hydroxycarboxylic acid for 3 to 180 minutes, washing the earthworm with water, and milling the earthworm.

(B-2) A method for producing a milled matter of an earthworm including steps of:
bringing a living earthworm into contact with a chloride of a metal selected from the group consisting of potassium, sodium, magnesium, and calcium,
subsequently immersing the living earthworm in a hydroxycarboxylic acid aqueous solution in which the pH is adjusted to 2 to 5, leaving the earthworm in the solution for 3 to 180 minutes, washing the earthworm with water, and milling the earthworm.

As a method for obtaining an extract of an earthworm, the following methods are preferable.

(C-1) A method for producing an extract of an earthworm including steps of:

bringing a living earthworm into contact with a chloride of at least one metal selected from the group consisting of potassium, sodium, magnesium, and calcium, subsequently bringing the living earthworm into contact with a powdery hydroxycarboxylic acid, diluting the hydroxycarboxylic acid with water to adjust the pH to 2 to 5, leaving the earthworm in the diluted hydroxycarboxylic acid for 3 to 180 minutes, washing the earthworm with water, milling the earthworm, dissolving the obtained milled matter in a freeze-dried form in water or an aqueous ethanol solution, and removing or separating an insoluble fraction.

(C-2) A method for producing an extract of an earthworm including the steps of:

bringing a living earthworm into contact with a chloride of a metal selected from the group consisting of potassium, sodium, magnesium, and calcium, subsequently immersing the living earthworm in a hydroxycarboxylic acid aqueous solution in which the pH is adjusted to 2 to 5, leaving the earthworm in the solution for 3 to 180 minutes, washing the earthworm with water, milling the earthworm, dissolving the obtained milled matter in a freeze-dried form in water or an aqueous ethanol solution, and removing or separating an insoluble fraction from the obtained solution.

Although the blending amount of dry powder, milled matter, and/or extract of an earthworm is not particularly limited, in the case of a liquid nasal drop composition, for example, the blending amount is, per 100 L of the nasal drop composition in terms of dry mass of the extract extracted with water, 0.1 to 100 mg, preferably 0.2 to 50 mg, and more preferably 1 to 20 mg.

EXAMPLES

Hereinbelow, the present invention will be described more specifically with reference to Examples. However, the present invention is not intended to be limited by Examples below. In Examples below, "percent (%)" is by mass unless otherwise specified.

(Aqueous Organic Substance Decomposition Product)

Forty liters of water was introduced into a reaction vessel containing 40 kg of earthworm *Lumbricus rubellus* castings and 15 kg of a wood material (Japanese cedar) (5 kg of woodchips and 10 kg of a blend of wood dusts and rice hulls), and then vaporized water was collected by a dehumidifier (DM-30, manufactured by Nakatomi Corporation) attached to the reaction vessel for about 1 day while stirring to obtain 15 to 20 L of a liquid. Ten to twenty liters of water was further added to the reaction vessel, then 10 kg of a wood material (Japanese cedar) (5 kg of woodchips and 5 kg of a blend of wood dusts and rice hulls) was added thereto, and then vaporized water was collected by the dehumidifier for about 1 day in the same manner to obtain 15 to 20 L of a liquid. About 40 L of a liquid (pH 8.71) prepared by mixing the obtained liquids was used as an aqueous organic substance decomposition product.

In the production of the above-described aqueous organic substance decomposition product, the water used was water prepared by purifying tap water with an SPG (Shirasu porous glass) permeable membrane (SPG Technology Co., Ltd.) and activated carbon.

(Earthworm Extract)

After leaving for 24 hours in a light place, 30 kg of living *Lumbricus rubellus* of which dirt was peeled from the skins were spread out to about 5 cm in the thickness on a flat plate, and 250 g of sodium chloride was evenly sprinkled on top of the earthworms. After 20 minutes, the earthworms were washed with water. Thereafter, 250 g of citric acid was sprinkled on the earthworms in the same manner, and then the citric acid was diluted by adding 30 liters of pure water in 15 seconds. At this time, the pH immediately after addition of water was 2.25, and the pH when completely diluted was 2.74. When sprinkled with citric acid powder, the earthworms released yellow body fluid at once. After the dilution of the citric acid with water, the earthworms were kept for 20 minutes in that state. Subsequently, the living earthworms were taken out from the soiled citric acid aqueous solution, washed with water, and milled at 10° C. using a homogenizer to prepare an earthworm paste. Next, after sucking and deaerating the earthworm paste to remove a gas contained therein, the earthworm paste was then placed on a stainless steel tray, instantaneously cooled to −35° C., and gradually frozen for 50 hours while maintaining this temperature. The frozen earthworm paste was kept at −35° C. and 0 Pa for 2 hours, the temperature was then raised to 25° C. at 40 Pa for 10 hours, the temperature was then raised to 40° C. at 35 Pa for 14 hours, the temperature was then raised to 65° C. at 35 Pa for 12 hours, and finally, the temperature was raised to 80° C. at 25 Pa for 6 hours to perform vacuum freeze drying. By this treatment, light yellow dry earthworm powder having a water content of 8% by mass was obtained.

25 g of the dry earthworm powder obtained as above was sampled, 500 mL of distilled water was added thereto, and the mixture was stirred at room temperature for 1 hour and extracted. The obtained extract was centrifuged (10,000×g, 4° C., 15 minutes), and a supernatant was collected to obtain an earthworm extract. The obtained earthworm extract was finely pulverized with a freeze vacuum dryer, sampled by 30 mg, and diluted with 500 mL of distilled water to obtain a stock solution.

(Nasal Drop Composition)

The aqueous organic substance decomposition product obtained above was diluted 5 times with water. The water used for the dilution was water prepared by purifying tap water with an SPG (Shirasu porous glass) permeable membrane (SPG Technology Co., Ltd.) and activated carbon.

The diluted aqueous organic substance decomposition product and the diluted stock solution of the earthworm extract obtained above were mixed at a ratio of 1,000:1 and passed through a 0.2 μm filter to obtain a nasal drop composition.

Example 1

<Pollinosis 1>

The symptoms of pollinosis of the subject below who was sprayed in the nasal cavities with the nasal drop composition obtained above in the form of mist 6 to 10 times per day, 2 to 5 sprays per application using a commercially available nasal irrigation spray on a daily basis were observed.

Subject: Female, 22 years old, disease duration: 2 years.
After 3 days, runny nose and tears decreased.
After 7 days, runny nose and tears stopped.
After 15 days, pain of pollinosis alleviated.
After 30 days, cured.

Example 2

<Pollinosis 2>

The symptoms of pollinosis of the subject below who was sprayed in the nasal cavities with the nasal drop composition obtained above in the form of mist 6 to 10 times per day, 2 to 5 sprays per application using a commercially available nasal irrigation spray on a daily basis were observed.

Subject: Male, 52 years old, disease duration: 15 years.
After 7 days, runny nose and eye itching decreased.
After 14 days, runny nose and itching disappeared.
After 25 days, the symptoms improved.
After 30 days, the symptoms disappeared.

Example 3

<Empyema 1>

The symptoms of empyema of the subject below who was sprayed in the nasal cavities with the nasal drop composition obtained above in the form of mist 6 to 10 times per day, 2 to 5 sprays per application using a commercially available nasal irrigation spray on a daily basis were observed.

Subject: Male, 18 years old, disease duration: 2 months, yellow runny nose.
After 7 days, amount and color of runny nose decreased.
After 10 days, runny nose stopped.
After 25 days, stuffy nose cleared, and the empyema cured.

Example 4

<Empyema 2>

The symptoms of empyema of the subject below who was sprayed in the nasal cavities with the nasal drop composition obtained above in the form of mist 6 to 10 times per day, 2 to 5 sprays per application using a commercially available nasal irrigation spray on a daily basis were observed.

Subject: Female, 15 years old, disease duration: 1 month.
After 3 days, runny nose decreased.
After 7 days, runny nose stopped.
After 15 days, stuffy nose cleared, and the empyema cured.

As shown in Examples 1 to 4, it was confirmed that a nasal drop composition suitable for treating or preventing a disease or symptom in the nasal cavities can be produced by collecting evaporated water generated from a mixture of earthworm castings and water.

The invention claimed is:

1. A method of treating or preventing a disease or symptom in a nasal cavity, comprising administering a nasal drop composition produced by a production method comprising:
    mixing earthworm castings with water to obtain a mixture; and
    collecting vaporized water generated from the mixture to obtain a liquid as the nasal drop composition.

2. The method according to claim 1, wherein the mixing further comprises mixing an organic substance together with the earthworm castings and the water.

3. The method according to claim 2, wherein the organic substance is a wood material.

4. The method according to claim 1, wherein the production method further comprises diluting the liquid with water to obtain the nasal drop composition.

5. The method according to claim 1, wherein the disease or symptom in the nasal cavity is pollinosis or empyema.

* * * * *